United States Patent [19]
Wyler

[11] 4,137,462
[45] Jan. 30, 1979

[54] PROBE FOR MEASURING STEAM QUALITY

[75] Inventor: John S. Wyler, Andover, Mass.

[73] Assignee: Westinghouse Electric Corp., Pittsburgh, Pa.

[21] Appl. No.: 846,943

[22] Filed: Oct. 31, 1977

[51] Int. Cl.$^2$ ............................................. G01N 21/26
[52] U.S. Cl. ..................... 250/573; 250/227
[58] Field of Search .................... 73/29; 250/227, 239, 250/216, 215, 573, 574, 575; 356/201, 207, 208

[56] References Cited

U.S. PATENT DOCUMENTS

| | | | |
|---|---|---|---|
| 3,618,061 | 11/1971 | Livers | 73/29 |
| 3,838,925 | 10/1974 | Marks | 250/573 |

Primary Examiner—David C. Nelms
Attorney, Agent, or Firm—J. W. Keen

[57] ABSTRACT

A probe for insertion into a steam flow which provides a quality measurement of the steam in that particular flow. Steam quality is determined by transmitting light across a portion of the steam flow, making a measurement of the light's intensity after traversing the steam flow, and comparing that intensity to light intensity which was measured through a dry steam flow. Light provided by a Helium-Neon laser is directed through a diverging lens which distributes the emitted light across a predetermined area. Such distributed light is directed through a light beam splitter which directs a portion of the light beam through a series of optic fibers. Such optic fibers transmit light through an isolation window, and across a steam flow specimen channel where it is reflected by a mirror. The reflected light from the mirror traverses the optic fibers in the opposite direction to light emitted from the laser. At least a portion of such oppositely directed light impinges on a photodetector which indicates the light's intensity passing through the steam channel and such integrity is compared to the light intensity which penetrates the steam channel flow specimen for completely dry steam. Fiber optics are used for transmitting the light over extended distances and in skewed, crooked directions. Conduits are provided for transporting non-condensible purging substances to the mirror's reflective surface and to the surfaces of the window barrier so as to prevent steam condensation thereon and avoid fallacious steam quality readings resulting therefrom.

8 Claims, 5 Drawing Figures

PROBE FOR MEASURING STEAM QUALITY

BACKGROUND OF THE INVENTION

1. Field of the Invention

This invention relates to measuring the performance of steam utilizing machines, and more particularly, to means for measuring steam quality or moisture at various points in a steam flow.

2. Description of the Prior Art

Determination of thermodynamic performance of steam utilizing apparatus requires measurement of thermodynamic state points at various points in the apparatus. Thermodynamic state points can be determined for dry steam from temperature and pressure measurements, but determination of state points for wet steam necessitates the ascertainment of the steam quality or moisture parameter. Steam turbines used for power generation require their thermodynamic and mechanical performance to be closely monitored. Thermodynamic performance monitoring provides an indication of the cost of turbine operation and gives early warning signals for many malfunctions. Steam quality in steam turbines is important to the mechanical performance since the moisture level at various locations in the turbine and at selected points along the blades is a very important parameter since moisture can cause blade erosion, corrosion-fatigue failures, and other mechanisms which can lead to mechanical failure of the turbine or its parts.

Calorimeters have, historically, been used to measure steam quality, but in recent years calorimetry has fallen into disrepute due to serious questions raised as to its accuracy. Aside from inaccuracy questions, calorimeters yield relatively slow quality determinations and, as such, cannot provide continuous quality monitoring. Such continuous monitoring is very important if quality measurement of steam in a thermodynamic machine is to be used for diagnostic and malfunction detection purposes.

A substantial part of the calorimeters' inherent inaccuracy results from the requirement of withdrawing a steam sample from the steam flow in question. Withdrawing such steam samples from the main steam flow exposes such withdrawn steam to a withdrawing probe permitting heat transfer therebetween and results in throttling of the steam sample between the main steam flow and the calorimeter or other instrument remotely situated from the main steam flow. An additional problem associated with such physically remote quality measuring devices is the necessity of being able to withdraw the steam sample from the steam vessel in a relatively straight line. Such straight line probe or quality measuring device restricts the turbine design and often necessitates a more complex assembly procedure than would otherwise be required. Other attempts to measure steam quality while avoiding withdrawing a steam sample include comparisons of light intensity penetrating the steam flow with those light intensities measured through dry steam flows. Such attempts often encountered "fogging" problems on transparent surfaces through which the measuring light beam normally passed. Such fogging resulted from steam condensation and caused inaccurate light intensity measurements.

Many of the problems associated with the prior art steam quality measuring apparatus stemmed directly from the straight line probe requirements and their inability to provide fast and continuous quality indications.

SUMMARY OF THE INVENTION

In accordance with the present invention an improved steam quality measuring device is provided for obtaining steam quality measurements continuously with higher accuracy than was heretofore possible without requiring a straight line measuring probe. The invention generally comprises a laser apparatus for emission of a primary light beam, means for splitting the primary light beam into a plurality of secondary light beams, a bundle of optical fibers capable of transmitting at least a portion of the secondary light beams therethrough, a specimen steam channel which routes steam across the path of the secondary light beams emitted by the optical fiber bundle, a mirror situated adjacent the specimen channel which reflects light directed thereto through the specimen channel, a transparent barrier situated between the optical fiber bundle and the specimen steam channel, means for preventing moisture formation on the transparent barrier and mirror, and a photodetector which provides a signal indicative of the reflected light's intensity. The quality of the steam passing through the specimen channel can be directly obtained by comparing photodetector signals for dry steam and the steam in question.

In a preferred embodiment of the invention a diverging lens is situated to receive light from the laser apparatus and distribute it across the entire optical fiber bundle. The moisture formation preventing means constitutes a series of conduits for transmitting purging substances to the mirror's reflective surface and the transparent barrier's surfaces for purging them of condensible substances and thus preventing fogging of those surfaces. The optical fiber bundle transmits light to and reflected light from the mirror and obviates the need for a straight line probe opening into the steam vessel which houses the steam flow in question. A portion of the reflected light transmitted through the optical fiber bundle is directed to the photodetector by the primary light beam splitting means.

The specimen channel and mirror are isolated from the remaining parts of the quality measuring apparatus by the transparent barrier which prevents moisture exposure of the optical fiber bundle. Relationships developed from Mie scattering theory permit steam quality determination from a knowledge of water droplets' mean diameter, laser wavelength, steam specimen pressure, light path length through the steam specimen, and comparison of light intensities between the steam mixture in question and dry steam after any appropriate light "noise" corrections have been applied and the photodetector's indicator preferably calibrated to account for such. Use of the present invention permits accurate steam quality measurement while avoiding the withdrawal of a steam specimen from the steam flow in question.

BRIEF DESCRIPTION OF THE DRAWINGS

The invention will be more fully understood from the following detailed description of a preferred embodiment taken in connection with the accompanying drawings, in which.

DESCRIPTION OF THE PREFERRED EMBODIMENT

The present invention is concerned primarily with steam quality measuring apparatus for steam utilizing devices. Accordingly, in the description which follows the invention is discussed in association with an axial flow steam turbine. It should be understood, however, that the invention may be utilized as a steam quality measuring apparatus in any steam utilizing device.

Figure 1:
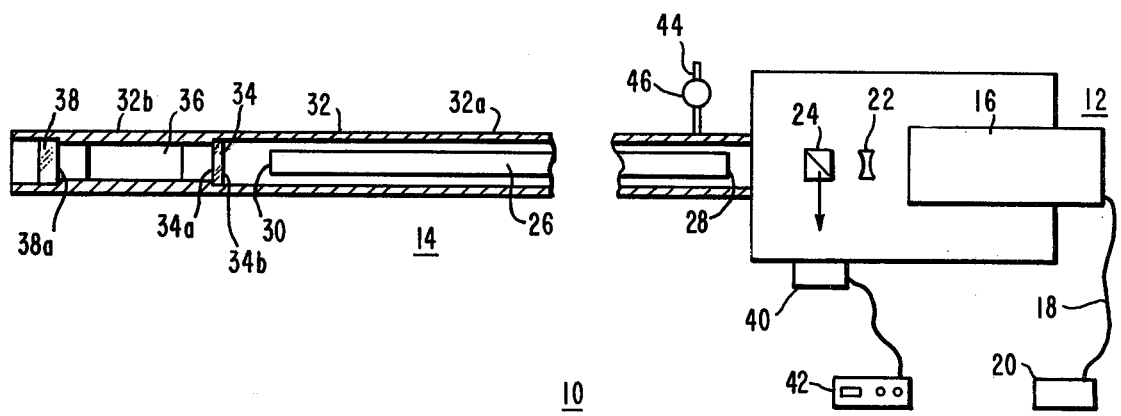
FIG. 1 is a transverse sectional view of an exemplary laser steam quality probe.

FIG. 1 illustrates a transverse sectional view of a steam quality measuring apparatus 10. Quality measuring apparatus 10 comprises a body portion 12 and probe portion 14. Situated within body portion 12 is a Helium-Neon laser 16 connected through leads 18 to power supply 20. A monochromatic light beam generated by laser 16 is dispersed across a predetermined cross-sectional area by diverging lens 22. Such dispersed light beam traverses beam splitter 24 where a portion of the dispersed light is directed radially outward, preferably toward light traps, and another portion of the dispersed light beam is directed into optical fiber bundle 26 which transmits light therethrough from end 28 to end 30. The optical fibers constituting optical fiber bundle 26 may follow skewed or crooked lines while transmitting light therethrough. Probe portion 14 has an outer tube structure or barrel 32 in which the optical fiber bundle is disposed. At axial end 30 of optical fiber bundle 26 is situated a transparent barrier or window 34. Light emitted from axial end 30 traverses barrier 34 and enters probe eye or specimen channel 36 through which the steam in question is allowed to flow. Moisture in the wet steam which passes through probe eye 36 obstructs a portion of the light transmitted thereto and prevents its traversal across the probe eye. The remainder of the light strikes mirror 38 which is preferably concave and reflects reversibly across probe eye 36. A portion of the reflected light will be obstructed and prevented from traversing probe eye 36, window 34, and optical fiber bundle 26 by the moisture present in the steam flowing through probe eye 36. The reflected light from mirror 38 which traverses optical fiber bundle 26 from end 30 to end 28 is directed to beam splitter 24 which routes a portion thereof to photodetector 40. Photodetector 40 causes a signal to be indicated on meter 42 with that indication representing the intensity of the light impinging on photodetector 40. Barrel 32 is seen to have two portions 32a and 32b which generally house the optical fiber bundle 26 and probe eye 36 respectively.

Purging fluid tap 44 and associated valve 46 are indicated as protruding from barrel portion 32a in the vicinity of body portion 12. Such purging fluid tap 44 permits entry therethrough of a non-refractive, non-condensible substance which is directed to faces 34a and 34b of window 34 and reflective face 38a of mirror 38 where such non-condensible substance blankets those surfaces and prevents contact therewith by steam or accompanying moisture passing through probe eye 36. Such purging substance prevents fogging of the surfaces 34a and 38a and thus avoids inaccurate light intensity indications by preventing portions of light directed thereto from being absorbed or diverted. To further augment the purging capability surfaces 34a and 38a are recessed from the edges of probe eye 36. Such recessing of surfaces 34a and 38a promotes a relatively thick layer of purging substance and thereby prevents any condensible substance penetration to those surfaces. Normal steam flow direction is shown by arrow 48. It has been found, however, that signals from photodetector meter 42 are relatively insensitive to the direction of steam flow through probe eye 36.

Figure 2A:
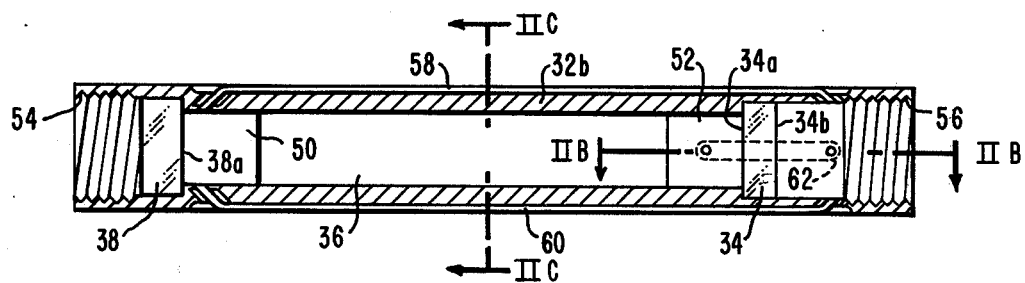
FIGS. 2A-2C are various sectional views of a portion of the laser steam probe.
Figure 2C:
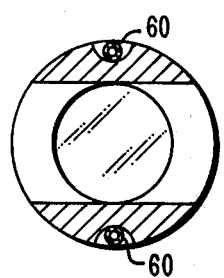
Figure 2B:
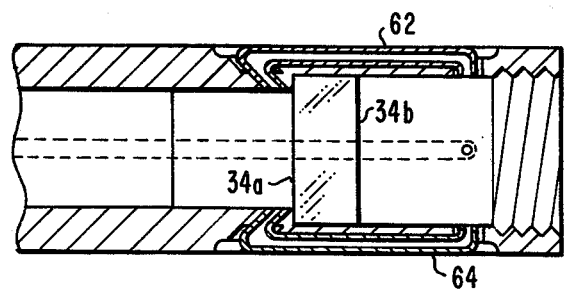

FIGS. 2A-2C illustrate various sectional views of barrel portion 32b and other elements situated therein. FIG. 2A is a transverse sectional view of barrel portion 32b which illustrates probe eye 36 bounded at each axial end by recess spaces 50 and 52 which respectively bound surfaces 38a and 34a of mirror 38 and barrier window 34. Axial ends 54 and 56 of barrel portion 32b are preferably threaded and capable of receiving therein a plug and externally threaded barrel portion 32a respectively. FIG. 2A also illustrates purging fluid conduits 58 and 60 which route purging fluid from the interior of barrel portion 32a to face 38a of mirror 38. Window 34 is seen to provide a transparent barrier between the interior of barrel portions 32a and 32b. Purging fluid conduits 62 and 64 are illustrated in FIG. 2B which is a sectional view taken from FIG. 2A. Purging fluid conduits 62 and 64 provide purging fluid to face 34a of window 34. Surface 34b of window 34 is maintained free of moisture by continuous contact with purging fluid which occupies the interior of barrel portion 32a with optical fiber bundle 26. FIG. 2C is an additional sectional view of FIG. 2A and illustrates the configuration of purging fluid conduit 60 within barrel portion 32b. It is to be understood that any purging fluid may be used which is non-condensible at the pressures and temperatures ordinarily used in steam utilizing devices such as steam turbine application. The steam quality in steam turbines usually falls below 100% only in the last two to four stages which are usually of a pressure lower than atmospheric. Due to the sub-atmospheric character of the steam pressure, it is very convenient to utilize atmospheric air as the purging fluid.

Barrel portion 32a is 101 inches in length by example and externally threaded on both axial ends while barrel portion 32b is 7¼ inches and is internally threaded on both axial ends. The internal threads on barrel portion 32b have already been discussed and the external threads on barrel portion 32a are for engagement with the internal threads at axial end 56 of barrel portion 32b and the internal threads (not shown) formed in body portion 12. The probe eye 36 is 4 inches long in the axial direction and its bounding separation spaces 50 and 52 are ½ inch in length by example. Barrel portions 32a and 32b are cylindrical in shape and have outside diameters of 0.8 inches and inside diameters of 0.56 inches. The purging fluid conduits 58, 60, 62, and 64 are, by example, 0.05 inches outside diameter and 0.03 inside diameter.

Figure 3:
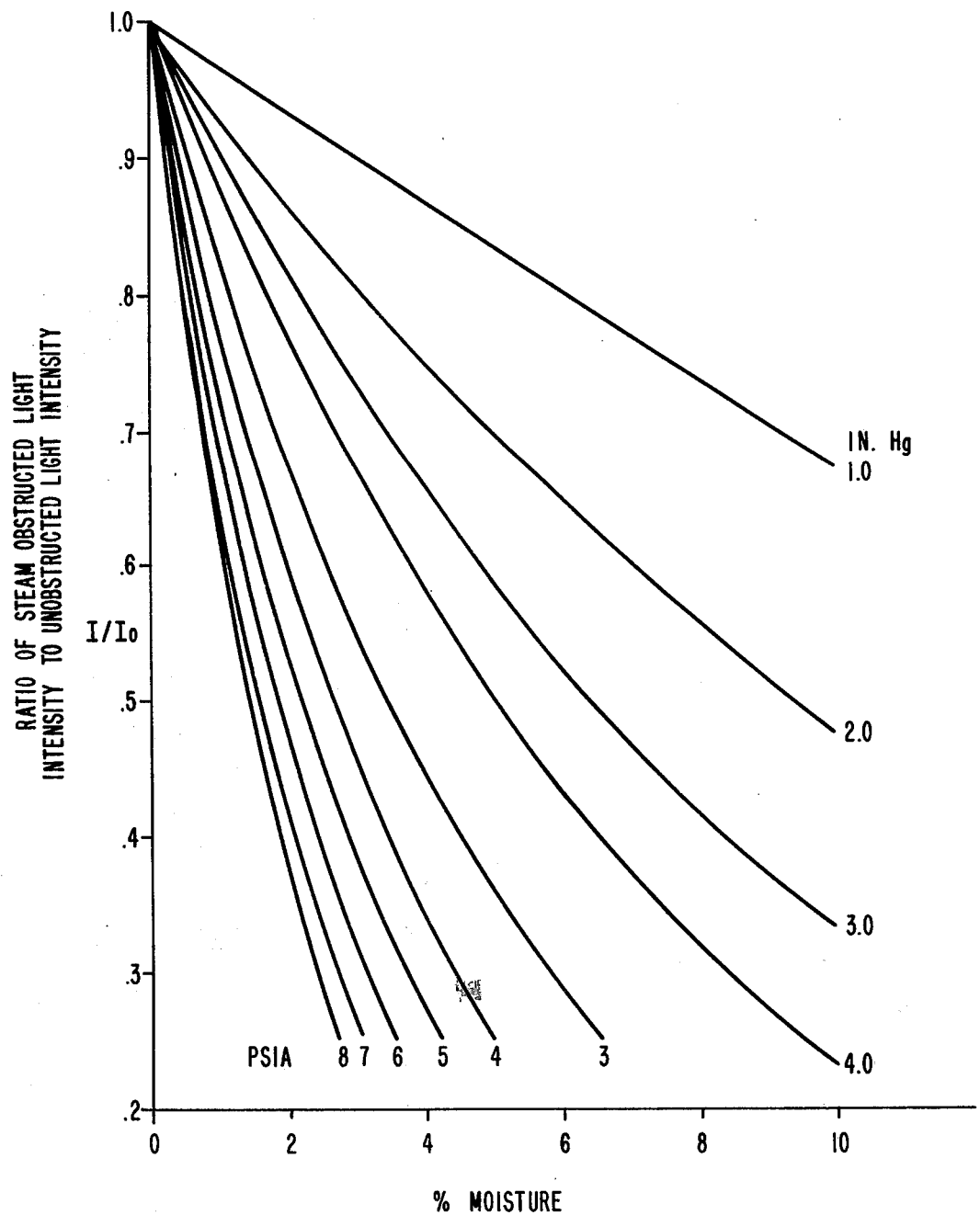
FIG. 3 is a plot of light intensity ratios versus steam moisture percentage for various steam pressures.

FIG. 3 is a plot of percent moisture (complement of quality) versus the ratio of light intensity in question to light intensity for dry steam. Several plots of varying steam mixture pressure are illustrated in FIG. 3. The plots illustrated in FIG. 3 were developed from Mie scattering theory which yields the following equation:

$$\frac{I}{I_o} = e^{-\frac{3}{2} \frac{\bar{E}}{D_{32}} \frac{V_f}{V_g} \frac{Y}{1-Y} t}.$$

The ratio of $I/I_o$ is the ratio of measured light intensity for a given steam mixture to the intensity of light which passes through dry steam. $\bar{E}$ and $D_{32}$ are the average extinction coefficient and Sauter mean diameter of moisture droplets respectively. It has been experimentally determined that $D_{32}$ for steam turbines is extremely close to 0.2 micrometers and such value was used as a constant in FIG. 3. $\bar{E}$ is known to be a function of the light's wavelength and $D_{32}$. Since a monochromatic light wavelength of known value (0.6328 micrometers) from a Helium-Neon laser was used and $D_{32}$ was experimentally obtained, $\bar{E}$ can then be determined. $V_f$ and $V_g$ are the respective specific volumes of the liquid and vapor phases of the steam mixture which can exist at the steam mixture's measured pressure. The light path's length through the specimen's steam is $t$ and which is set by the width of the specimen channel which, in this case, is 8 inches (2×4 inches). Using the aforementioned, already determined parameters and measuring the ratio of $I/I_o$ permits calculation of Y which is the steam quality. The plots shown in FIG. 3 have constant parameters of a light source wavelength of 0.6328 micrometers and Sauter mean diameter of 0.2 micrometers.

In practice, steam quality or its complement steam moisture is determined by measuring the light intensity ratio and using such measurement in association with the plot illustrated in FIG. 3. The light intensity indications must usually be corrected since there is often a small zero offset of the readings due to reflections from various optical surfaces, but such extraneous indications or "light noise" can be easily determined and corrected for by blocking the probe eye 36 and noting the light intensity indication at that time. Although the measured light intensity ratio has been discussed in conjunction with plots of it versus moisture percentage for various steam mixture pressures, it is to be understood that such moisture or steam quality could be directly obtained from suitable automated equipment such as a computer which has been appropriately programmed and which accepts the required input parameters. Thus, while only a light intensity meter 42 is shown in FIG. 1, an additional instrument could be connected thereto and caused to yield the quality measurements directly.

It will now be apparent that an improved steam quality measurement apparatus has been provided which has a flexible probe capable of deforming around bracing and other objects and which provides accurate steam quality measurements without withdrawing a sample of the steam while avoiding light intensity error measurement from fogging of transparent and reflective structures.

I claim:

1. A steam quality measuring apparatus comprising:
 a laser apparatus from which a primary light beam is emittable;
 means for splitting the primary light beam into a plurality of secondary light beams, said primary light beam being receivable from said laser;
 a bundle of optical fibers which transmit at least one of said secondary light beams therethrough from a first end adjacent said splitting means to a second end;
 a specimen steam channel for routing steam across the path of said secondary light beam;
 a mirror disposed adjacent said specimen channel for reflecting light directed thereto through said specimen channel from said optical fibers;
 a substantially transparent barrier for transmitting light emitted by said optical fiber bundle therethrough, said mirror and specimen steam channel being isolated from the optical fiber bundle by said transparent barrier wherein said barrier has a first surface adjacent said specimen channel;
 means for preventing moisture formation on said transparent barrier and mirror; and
 a photodetector which provides a signal indicative of the intensity of the reflected light directed thereto from said mirror, said reflected light's intensity being characteristic of the steam's quality.

2. The steam quality measuring apparatus of claim 1 wherein said mirror's reflecting face is concave.

3. The steam quality measuring apparatus of claim 1, said moisture preventing means comprising:
 conduit means for transmitting fluids therethrough which purge condensible substances from the mirror's reflective surface and the transparent barrier's first surface.

4. The steam quality measuring apparatus of claim 1 wherein reflected light from said mirror traverses said optical fibers from said second to said first end with at least a portion of said light being diverted by said splitting means to said photodetector.

5. The steam quality measuring apparatus of claim 1, further comprising:
 a diverging lens for distributing light entering said optical fiber bundle across the entire bundle.

6. The steam quality measuring apparatus of claim 5 wherein said diverging lens is disposed to receive light from said laser and transmit it to said light beam splitting means.

7. The steam quality measuring apparatus of claim 5 wherein said diverging lens is disposed to receive light from said light beam splitting means and transmit it to the optical fiber bundle.

8. The steam quality measuring apparatus of claim 1 wherein said mirror and said transparent barrier are separated from said specimen channel by predetermined distances.

* * * * *